(12) United States Patent  
Woodward et al.

(10) Patent No.: US 8,986,715 B2  
(45) Date of Patent: *Mar. 24, 2015

(54) METHOD OF ENHANCING HAIR GROWTH

(71) Applicant: Allergan, Inc., Irvine, CA (US)

(72) Inventors: David F. Woodward, Lake Forest, CA (US); Amanda M. VanDenburgh, Huntington Beach, CA (US)

(73) Assignee: Allergan, Inc., Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/300,902

(22) Filed: Jun. 10, 2014

(65) Prior Publication Data

US 2014/0296345 A1  Oct. 2, 2014

Related U.S. Application Data

(63) Continuation of application No. 13/937,512, filed on Jul. 9, 2013, which is a continuation of application No. 13/441,783, filed on Apr. 6, 2012, now Pat. No. 8,632,760, which is a continuation of application No.

(Continued)

(51) Int. Cl.
*A61K 9/00* (2006.01)
*A61K 8/42* (2006.01)

(Continued)

(52) U.S. Cl.
CPC .............. *A61K 8/42* (2013.01); *A61K 31/165* (2013.01); *A61K 31/557* (2013.01); *A61K 31/558* (2013.01); *A61Q 7/00* (2013.01); *A61Q 7/02* (2013.01)
USPC ....................................................... 424/400

(58) Field of Classification Search
CPC ..................................................... A61K 35/36
See application file for complete search history.

(56) References Cited

U.S. PATENT DOCUMENTS 3,382,247 A  5/1968 Anthony et al.
3,644,363 A  2/1972 Kim (Continued)

FOREIGN PATENT DOCUMENTS

CA  1208560  7/1986
CA  2144967  3/1994

(Continued)

OTHER PUBLICATIONS

U.S. Appl. No. 90/009,431, filed Mar. 10, 2009, Murray Johnstone.

(Continued)

*Primary Examiner* — Paul Dickinson
(74) *Attorney, Agent, or Firm* — Lorenz Siddiqi

(57) ABSTRACT

Methods and compositions for stimulating the growth of hair are disclosed wherein said compositions include a cyclopentane heptanoic acid, 2-cycloalkyl or arylalkyl compound represented by the formula I

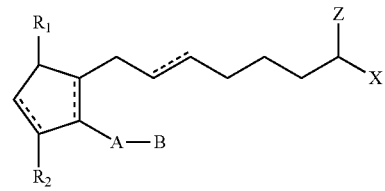

wherein the dashed bonds represent a single or double bond which can be in the cis or trans configuration, A, B, Z, X, $R_1$ and $R_2$ are as defined in the specification. Such compositions are used in treating the skin or scalp of a human or non-human animal. Bimatoprost is preferred for this treatment.

20 Claims, 1 Drawing Sheet

Related U.S. Application Data

13/356,284, filed on Jan. 23, 2012, now Pat. No. 8,263,054, which is a continuation of application No. 12/425,933, filed on Apr. 17, 2009, now Pat. No. 8,298,518, which is a continuation of application No. 11/943,714, filed on Nov. 21, 2007, now Pat. No. 8,038,988, which is a continuation of application No. 11/805,122, filed on May 22, 2007, now Pat. No. 8,101,161, which is a continuation of application No. 10/345,788, filed on Jan. 15, 2003, now Pat. No. 7,351,404.

(60) Provisional application No. 60/354,425, filed on Feb. 4, 2002.

(51) Int. Cl.
*A61K 31/165* (2006.01)
*A61K 31/557* (2006.01)
*A61K 31/558* (2006.01)
*A61Q 7/00* (2006.01)
*A61Q 7/02* (2006.01)

(56) References Cited

U.S. PATENT DOCUMENTS

| | | |
|---|---|---|
| 4,128,577 A | 12/1978 | Nelson |
| 4,139,619 A | 2/1979 | Chidsey |
| 4,311,707 A | 1/1982 | Birnbaum et al. |
| 4,543,353 A | 9/1985 | Faustini et al. |
| 4,596,812 A | 6/1986 | Chidsey et al. |
| 4,599,353 A | 7/1986 | Bito |
| 4,812,457 A | 3/1989 | Narumiya et al. |
| 4,839,342 A | 6/1989 | Kaswan |
| 4,883,581 A | 11/1989 | Dickakian |
| 4,888,354 A | 12/1989 | Chang et al. |
| 4,889,845 A | 12/1989 | Ritter et al. |
| 4,952,581 A | 8/1990 | Bito et al. |
| 4,968,812 A | 11/1990 | Wang et al. |
| 5,001,153 A | 3/1991 | Ueno et al. |
| 5,194,429 A | 3/1993 | Ueno et al. |
| 5,280,018 A | 1/1994 | Ritter et al. |
| 5,288,754 A | 2/1994 | Woodward et al. |
| 5,296,504 A | 3/1994 | Stjernschantz et al. |
| 5,321,128 A | 6/1994 | Stjernschantz et al. |
| 5,352,708 A | 10/1994 | Woodward et al. |
| 5,422,368 A | 6/1995 | Stjernschantz et al. |
| 5,422,369 A | 6/1995 | Stjernschantz et al. |
| 5,431,881 A | 7/1995 | Palacios |
| 5,474,979 A | 12/1995 | Ding et al. |
| 5,480,900 A | 1/1996 | DeSantis et al. |
| 5,508,303 A | 4/1996 | Isogaya et al. |
| 5,510,383 A | 4/1996 | Bishop et al. |
| 5,545,655 A | 8/1996 | Friedlander et al. |
| 5,578,618 A | 11/1996 | Stjernschantz et al. |
| 5,578,643 A | 11/1996 | Hanson et al. |
| 5,607,978 A | 3/1997 | Woodward et al. |
| 5,688,819 A | 11/1997 | Woodward |
| 5,698,733 A | 12/1997 | Hellberg et al. |
| 5,773,472 A | 6/1998 | Stjernschantz et al. |
| 5,789,244 A | 8/1998 | Heidrun et al. |
| 6,025,392 A | 2/2000 | Selliah et al. |
| 6,124,344 A | 9/2000 | Burk |
| 6,160,129 A | 12/2000 | Burk |
| 6,232,344 B1 | 5/2001 | Feng et al. |
| 6,254,860 B1 | 7/2001 | Garst |
| 6,258,844 B1 | 7/2001 | Garst et al. |
| 6,262,105 B1 | 7/2001 | Johnstone |
| 6,350,442 B2 | 2/2002 | Garst |
| 6,403,649 B1 | 6/2002 | Woodward |
| 6,441,047 B2 | 8/2002 | DeSantis |
| 7,351,404 B2 | 4/2008 | Woodward et al. |
| 7,368,436 B2 | 5/2008 | Gleave et al. |
| 7,388,029 B2 | 6/2008 | DeLong et al. |
| 7,514,474 B1 | 4/2009 | Lipkin et al. |
| 8,038,988 B2 | 10/2011 | Woodward et al. |
| 8,101,161 B2 | 1/2012 | Woodward et al. |
| 2002/0044953 A1 | 4/2002 | Michelet et al. |
| 2002/0103255 A1 | 8/2002 | Hellberg et al. |
| 2002/0172693 A1 | 11/2002 | DeLong et al. |
| 2003/0083381 A1 | 5/2003 | Kumagai et al. |
| 2003/0147823 A1 | 8/2003 | Woodward et al. |
| 2003/0199590 A1 | 10/2003 | Cagle et al. |
| 2004/0052760 A1 | 3/2004 | Michelet et al. |
| 2005/0222232 A1 | 10/2005 | DeLong et al. |
| 2007/0078175 A1 | 4/2007 | Boulle et al. |
| 2007/0160562 A1 | 7/2007 | Brinkenhoff |
| 2008/0070988 A1 | 3/2008 | Woodward et al. |
| 2008/0275118 A1 | 11/2008 | Shaw et al. |
| 2009/0018204 A1 | 1/2009 | Brinkenhoff |
| 2009/0270392 A1 | 10/2009 | Old et al. |
| 2011/0002866 A1 | 1/2011 | Lubit et al. |
| 2011/0112198 A1 | 5/2011 | Gore et al. |

FOREIGN PATENT DOCUMENTS

| | | |
|---|---|---|
| CA | 2174655 | 4/1995 |
| CA | 1339132 | 7/1997 |
| EP | 0170258 | 2/1986 |
| EP | 0249194 | 12/1987 |
| EP | 0308135 | 3/1989 |
| EP | 0639563 | 2/1995 |
| FR | 2239458 | 7/1973 |
| JP | S49-069636 | 7/1974 |
| JP | 61-218510 | 9/1986 |
| JP | H05-0331025 | 12/1993 |
| JP | H09-295921 | 11/1997 |
| JP | 10-287532 | 10/1998 |
| WO | 98-33497 | 8/1979 |
| WO | 89-03384 | 4/1989 |
| WO | 95-11003 | 4/1995 |
| WO | 97-31895 | 9/1997 |
| WO | 99-12895 | 3/1999 |
| WO | 00-54810 | 9/2000 |
| WO | 01-74307 | 10/2001 |
| WO | 01-74315 | 10/2001 |
| WO | 2007-143568 | 12/2007 |
| WO | 2009-011744 | 1/2009 |
| WO | 2011-119748 | 9/2011 |
| WO | 2012-068515 | 5/2012 |

OTHER PUBLICATIONS

U.S. Appl. No. 90/009,430, filed Mar. 15, 2009, David Woodward.
Abramovitz, Mark et al, The Utilization of Recombinant prostanoid Receptors to Determine the Affinities and Selectivities of Prostaglandins and Related Analogs, Biochimica et Biophysica Acta, 2000, 285-293, 1483.
Abramovitz, Mark, Cloning and Expressing of a cDNA for the Human prostanoid FP Receptor, Journal of Biological Chemistry, 1994, 2632-2636, 269(4).
Adis Data Information, ZD 6416, 2003.
Adis, Alprostadil (NexMed) Alprox-TDTM, BefarTM, FemproxTM, Prostaglandin E1 (NewMed), Adis R & D Profile, 1999, 413-414, 2(6), Adis International Limited.
Al-Sereiti, M.R., Pharmacology of Rosemary (*Rosmarinus officinalis* Linn.) and its Therapeutic Potentials, Indian Journal of Experimental Biology, 1999, 124-130, 37.
Allenby, A.C. et al, Mechanism of Action of Acclerants on Skin Penetration, Br. J. Derm, 1969, 47-55, 81(Supp. 4).
Allergan Clinical Study Report, 192024-008, 2000.
Allergan, Inc., Dermatologic and Ophthalmic Drugs Advisory Committee Briefing Document for Bimatoprost Solution 0.03%, Dermatologic and Ophthalmic Drugs Advisory Committee Briefing Document for Bimatoprost Solution 0.03%, Oct. 29, 2008, 1-108.
Alm, Albert et al, Effects on Intraocular Pressure and Side Effects of 0.005% Latanoprost Applied Once Daily, Evening or Morning, Ophthalmology, 1995, 1743-1752, 102.
Alm, Albert et al, Phase III Latanoprost Studies in Scandinavia, the United Kingdom and the United States, Survey of Ophthalmology, Feb. 1997, S105-S110, 41(2).
Alm, Albert et al, Uveoscleral Outflow—A Review, Experimental Eye Research, 2009, 760-768, 88(4).

(56) References Cited

OTHER PUBLICATIONS

Alm, Albert, The Potential of Prostaglandin Derivates in Glaucoma Therapy, Current Opinion in Ophthalmology, 1993, 44-50, 4(11).
Audoly, Laurent et al, Identification of Specific EP Receptors Responsible for the Hemodynamic Effects of PGE2, Am. J. Physiol., 1999, H924-H930, 277.
Badawy, Sherif et al, Salt Selection for Pharmaceutical Compounds, Preformulation in Solid Dosage Form Development (Informa Healthcare), 2008, 63-80, Chapter 2.3, Adeyeyem, Moji, ed.
Bartmann, W., Synthesis and Biological Activity, Luteolytic Prostaglandins, Feb. 1979, 301-311, 17(2).
Bastin, Richard et al, Salt Selection and Optimisation Procedures for Pharmaceutical New Chemical Entities, Organic Process Research & Development, 2000, 427-435, 4.
Bean, Gerald, Commercially Available Prostaglandin Analogs for the Reduction of Intraocular Pressure: Similarities and Differences, Survey of Ophthalmology, 2008, S69-S84, 53 (Supp. 1).
Berge, Stephen M., Pharmaceutical Salts, Journal of Pharmaceutical Sciences, Jan. 1977, 1-19, 66 (1), US.
Berglund, Barbara et al, Investigation of Structural Analogs of Prostaglandin Amides for Binding to and Activation of CB1 and CB2 Cannabinoid Receptors in Rat Brain and Human Tonsils, Adv Exp Med Biol, 1999, 527-533, 469.
Bird, Katie, Nano Carriers Enhance Skin Penetration and Antioxidant Effect of CoQ10, Cosmetics design-asia.com, Apr. 8, 2010, 1 Page, n/a, William Reed Business Media SAS.
Bito, L.Z. et al, Long-Term Maintenance of Reduced Intraocular Pressure by Daily or Twice Daily Topical Application of Prostaglandins to Cat or Rhesus Monkey Eyes, Investigative Ophthalmology & Visual Science, 1983, 312-319, 24(3).
Bito, Laszlo, A new approach to the medical management of glaucoma, from the bench to the clinic, and beyond, Investigative Ophthalmology & Visual Science, 2001, 1126-1133, 42(6), The Proctor Lecture.
Brandt, James et al, Comparison of Once- or Twice-Daily Bimatoprost with Twice-Daily Timolol in Patients with Elevated IOP, American Academy of Ophthalmology, 2001, 1023-1031, 108(6).
Brandt, James, PA022 Phase III, 3-month Comparison in Timolol with AGN-192024: A New Ocular Hypotensive Lipid for Glaucoma Management, Presented at 2000 Am. Acad. Ophthalmology, Ann. Mtg., Oct. 23, 2000, 1 Page.
Brubaker, Richard et al, Effects of AGN 192024, a new Ocular Hypotensive Agent, on Aqueous Dynamics, American journal of Ophthalmology, 2001, 19-24, 131(1).
Bundy, Gordon, Synthesis of 17-Phenyl-18, 19, 20-Trinorprostaglandins I. The PG1 Series, Prostaglandins, 1975, 1-4, 9(1).
Business Wire, Phase III Lumigan, AGN-192024—Data Presented At American Academy of Ophthalmology, American Academy of Ophthalmology, 2000, 1-3, Retrieved Dec. 14, 2010.
Cadet, Patrick et al, Molecular Identification and Functional Expression of µ3, a Novel Alternatively Spliced Variant of the Human µ Opiate Receptor Gene, J. Immunol., 2003, 5118-5123, 170.
Camras, Carl B. et al, Bimatoprost, the Prodrug of a Prostaglandin Analogue, Br J Ophthalmol, 2008, 862-863, 92.
Camras, Carl B. et al, Comparison of Latanoprost and Timolol in Patients with Ocular Hypertension and Glaucoma, Ophthalmology, 1996, 138-147, 103(1).
Camras, Carl B. et al, Detection of the Free Acid of Bimatoprost in Aqueous Humor Samples From Human Eyes Treated with Bimatoprost Before Cataract Surgery, The American Academy of Ophthalmology, 2004, 2193-2198, 7pg.
Camras, Carl B. et al, Latanoprost, a prostaglandin Analog, for Glaucoma Therapy, Ophthalmology, 1996, 1916-1924, 103(11).
Camras, Carl B. et al, Multiple Dosing of Prostaglandin F2α or Epinephrine on Cynomolgus Monkey Eyes, Investigative Ophthalmology & Visual Science, Sep. 1988, 1428-1436, 29(9).
Camras, Carl B. et al, Multiple Dosing of Prostaglandin F2α or Epinephrine on Cynomolgus Monkey Eyes, Investigative Ophthalmology & Visual Science, 1987, 463-469, 28(3).
Camras, Carl B. et al, Multiple Dosing of Prostaglandin F2α or Epinephrine on Cynomolgus Monkey Eyes, Investigative Ophthalmology & Visual Science, 1987, 921-926, 28(6).
Camras, Carl B. et al, Reduction of Intraocular Pressure in Normal and Glaucomatous Primate (*Aotus trivirgatus*) Eyes by Topically Applied Prostaglandin F2α, Current Eye Research, 1981, 205-209, 1 (4).
Cantor, Louis et al, Levels of Bimatoprost Acid in the Aqueous Humour After Bimatoprost Treatment of Patients with Cataract, Br. J. Ophthalmol, 2007, 629-632, 91.
Cantor, Louis et al, Reply-Bimatoprost, the Prodrug of a Prostaglandin Analogue, Br J Ophthalmol, 2008, 863-864, 92.
CAS RN 155206-00-1 May 20, 1994.
Cayatte, Antonio et al, The Thromboxane A2 Receptor Antagonist, S18886, Decreases atherosclerotic Lesions and serum Intracellular Adhesion Molecule-1 in the Apo E Knockout Mouse, 71st Scientific Sessions, 1998, I-115 (Abstract), 98(17).
Chen, June et al, AGN 191129: A Neutral Prostaglandin F2n (PGF2n) Analog That Lacks the Mitogenic and Uterotonic Effects Typical of FP Receptor Agonists, Glaucoma, Anatomy & Pathology, Physiology & Pharmacology, 1999, 3562-B420, 40(4).
Chen, June et al, Replacement of the Carboxylic Acid Group of Prostaglandin F2α (PGF2α) with Certain Non-Ionizable Substituents Results in Pharmacologically Unique Ocular Hypotensive Agents, 11th Intl Conf. Advances Prostaglandin & Leukotriene Res.: Basic Sci. & New Clinical Applications—Abstract Book, 2000, 1 page.
Chen, June et al, Studies on the Pharmacology of Prostamide F2α, A Naturally Occurring Substance, Brit. J. Pharmacology, 2001, 63P, 133.
Chyun, Yong et al, Stimulation of Bone Formation by Prostaglandin E2, Prostaglandins, 1984, 97-103, 27(1).
Clissold, D., The Potential for Prostaglandin Pharmaceuticals, Lipids in Health and Nutrition, 1999, 115-129, 244, The Royal Society of Chemistry.
Cohen, Joel, Enhancing the Growth of Natural Eyelashes: The Mechanism of Bimatoprost-Induced Eyelash Growth, Dermatol Surg, 2010, 1361-1371, 36(9).
Coleman, Robert et al, Prostanoids and Their Receptors, Comprehensive Medicinal Chemistry, 1990, 643-714, 3.
Coleman, Robert, VIII. International union of Pharmacology Classification of Prostanoid Receptors: Properties, Distribution, and Structure of the Receptors and Their Subtypes, The American Society for Pharmacology and Experimental Therapeutics, 1994, 205-229, 26(2).
Collins, Paul et al, Synthesis of Therapeutically Useful Prostaglandin and Prostacyclin Analogs, Chem. Rev., 1993, 1533-1564, 93.
Colombe, Laurent et al, Prostaglandin metabolism in human hair follicle, Experimental Dermatology, May 16, 2007, 762-769, 16, US.
Corsini, A. et al, (5Z)-Carbacyclin Discriminates Between Prostacyclin-Receptors Coupled to Adenylate Cyclase in Vascular Smooth Muscle and Platelets, Br. J. Pharmac., 1987, 255-261, 90.
Cox, Colin et al, Protein Fabrication Automation, Protein Science, 2007, 379-390, 16.
Crowston, Jonathan et al, Effect of Bimatoprost on Intraocular Pressure in prostaglandin FP Receptor Knockout Mice, Investigative Ophthalmology & Visual Science, 2005, 4571-4577, 46.
Darnell, J., Cell-to-Cell Signaling: Hormones and Receptors, Molecular Cell Biology, 1990, 738-743, vol. 82, Darnell, J., Lidish, H., Baltimore, D., Eds., New York, New York.
Davies, Sean, Hydrolysis of Bimatoprost (Lumigan) to Its Free Acid by Ocular Tissue In Vitro, Journal of Ocular Pharmacology and Therapeutics, 2003, 45-54, 19(1).
De Asua, L Jimenez et al, The Stimulation of the Initiation of DNA Synthesis and Cell Division in Swiss Mouse 3T3 Cells by Prostaglandin F2α Requires Specific Functional Groups in the Molecule, J. Biol. Chemistry, 1983, 8774-8780, 256(14).
Dean, T.R. et al, Improvement of Optic Nerve Head Blood Flow After One-Week Topical Treatment with Travoprost (AL06221) In The Rabbit, Investigative Ophthalmology & Visual Science, Mar. 15, 1999, 2688-B563, 40(4).

(56) References Cited

OTHER PUBLICATIONS

Del Toro, F. et al, Characterization of Prostaglandin E2 Receptors and Their Role in 24,25-(OH)2D3-Mediated Effects on Resting Zone Chondrocytes, Journal of Cellular Physiology, 2000, 196-208, 182.

Delong, Mitchell, Prostaglandin Receptor Ligands: Recent Patent Activity, IDrugs, 2000, 1039-1052, 3(9).

Depperman, William, Up-To-Date Scalp Tonic, Book Reviews, 1970, 1115, 283(20).

Dirks, Monte et al, Efficacy and Safety of the Ocular Hypotensive Lipid™ 192024 in Patients with Elevated IOP: A 30-Day Comparison with Latanoprost, Investigative Ophthalmology & Visual Science, Mar. 15, 2000, S514, 41(4).

Dubiner, Harvey, Efficacy and Safety of Bimatoprost in Patients With Elevated Intraocular Pressure: a 30-Day Comparison With Latanoprost, Surv. Ophthalmol, 2001, S353-S560, 45 (4).

Easthope, Stephanie et al, Topical Bimatoprost, Drug Aging, 2002, 231-248, 19(3).

Eisenberg, Dan et al, A Preliminary Risk-Benefit Assessment of Latanoprost and Unoprostone in Open-Angle Glaucoma and Ocular Hypertension, Drug Safety, 1999, 505-514, 20(6).

Ellis, Cathy et al, Metabolism of Prostaglandin D2 in the Monkey, The Journal of Biological Chemistry, 1979, 4152-4163, 254(10).

Emu Oil Hairloss and Frontal Regrowth, 2010, 4 Pages, www.hairloss-research.org/blog/?p=73.

Enyedi, Laura et al, The Effectiveness of Latanoprost for the Treatment of Pediatric Glaucoma, J AAPOS, 1999, 33-39, 3(1).

Ezure, T. et al, Involvement of Sonic Hedgehog in Cyclosporine A Induced Initiation of Hair Growth, Journal of Dermatological Science, 2007, 168-170, 47.

Fagot, Dominique et al, Mitogenic Signaling by Prostaglandins in Chemically Transformed Mouse Fibroblasts: Comparison with Phorbol Esters and Insulin, Endocrinology, 1993, 1729-1734, 132(4).

Fall, P.M., Inhibition of Collagen Synthesis by Prostaglandins in the Immortalized Rat Ostroblastic Cell Line Pyla: Structure-Activity Relations and Signals Transduction Mechanisms, J. Bone Miner Res., 1994, 1935-1943, 9(12).

Fang, Jia-You et al, In Vitro and in Vivo Evaluations of the Efficacy and Safety of Skin Permeation Enhancers Using Flurbiprofen as a Model Drug, International Journal of Pharmaceutics, 2003, 153-166, 255.

Faulkner, Robert, Aqueous Humor Concentrations of Bimatoprost Free Acid, Bimatoprost and Travoprost Free Acid in Cataract Surgical Patients administered Multiple Topical Ocular Doses of Lumigan or Travatan, Journal of Ocular Pharmacology and Therapeutics, 2010, 147-156, 26(2).

FDA Approves Two New intraocular Pressure Lowering Drugs for the Management of Glaucoma, Mar. 16, 2001, FDA News.

FDA Label for Approved NDA 22-184 of Lumigan 0.01% and Lumigan 0.03%, Aug. 31, 2010.

Fiscella, Richard, Peek into the Drug Pipeline, Review of Optometry Online, Jan. 15, 2001, 5 pages.

Fitzpatrick, F.A., Separation of Prostaglandins and Thromboxanes by Gas Chromatography with Glass Capillary Columns, Analytical Chemistry, 1978, 47-52, 50(1).

Flisiak, Robert et al, Effect of Misoprostol on the Course of Viral Hepatitis B, Hepato-Gastroenterology, 1997, 1419-1425, 44.

Frenkel, R E et al, Evaluation of Circadian Control of Intraocular Pressure After a Single Drop of Bimatoprost 0.03% or Travoprost 0.004%, Curr. Med. Res. Opin., Apr. 2008, 919-923, 24(4).

Funk, Colin et al, Cloning and Expression of a cDNA for the Human Prostaglandin E Receptor EP1 Subtype*, The Journal of Biological Chemistry, Dec. 15, 1993, 26767-26772, 268(35).

Gandolfi, Stefano, Three-month Comparison of Bimatoprost and Latanoprost in Patients With Glaucoma and Ocular Hypertension, Adv. Ther., 2001, 110-121, 18.

Garadi, R et al, Travoprost: A New Once-Daily Dosed Prostaglandin for The Reduction of Elevated Intraocular Pressure, Investigative Ophthalmology & Visual Science, 1999, 4378-B181, Abstract.

Geng, Ling et al, Misoprostol, A PGE1 Analog That is Radioprotective for Murine Intestine and Hair, Induces Widely Different Cytokinetic Changes in These Tissues, The Journal of Investigative Dermatology, 1996, 858, 106(4).

Geng, Ling et al, Topical or Systemic 16,16 dm Prostaglandin E2 or WR-2721 (WR-1065) Protects Mice From Alopecia After Fractionated Irradiation, Int. J. Radiat. Biol., 1992, 533-537, 61(4).

Gerth, Jeff et al, Drug Makers Reap Profits on Tax-Backed Research, Apr. 23, 2000, 10 pages, New York Times.

Giuffre, Giuseppe, The Effects of Prostaglandin F2α in the Human Eye, Graefe's Archive Clin. & Exper. Ophthal., 1985, 139-141, 222.

Green Tea Consumption Grows Hair, Protects Against UV Radiation in Animal Models, 2010, 4 Pages, www.hairloss-research.org/blog/?p=4.

Grice, Jeffrey et al, Relative Uptake of Minoxidil into Appendages and Stratum Corneum and Permeation Through Human Skin in Vitro, Journal of Pharmaceutical Sciences, Feb. 2010, 712-718, 99(2).

Griffin, Brenda et al, AL-8810: A Novel Prostaglandin F2α Analog with Selective Antagonist Effects at the Prostaglandin F2α (FP) Receptor, Journal of Pharmacology and Experimental Therapeutics, 1999, 1278-1284, 290(3).

Grow (Verb) Definition, Merriam Webster's Dictionary, Retrieved from http://www.merriam-webster.com/dictionary/growing on Jul. 9, 2012.

Hall, Alistair et al, Clinprost Tijin, Current Opinion in Cardiovascular, Pulmonary & Renal Investigational Drugs, 1999, 605-610, 1(5).

Hallinan, Ann et al, Aminoacetyl Moiety as a Potential Surrogate for Diacylhydrazine Group of SC-51089, a Potent PGE2 Antagonist, and Its Analogs, J Med Chem, 1996, 609-613, 39.

Hanson, W R et al, 16,16 dm Prostaglandin2 Protects From Acute Radiation-Induced Alopecia in Mice, Clinical Research, 1988, 906A, 36(6).

Hanson, W R et al, Subcutaneous or Topical Administration of 16,16 Dimethyl Prostaglandin E2 Protects From Radiation-Induced Alopecia in Mice, Int. J. Radiation Oncology Biol. Phys., 1992, 333-337, 23.

Hartke, J.R. et al, Prostanoid FP Agonists Build Bone in the Ovariectomized Rat, Prostanoid FP Agonists Build Bone in the Ovariectomized Rat, 1999, S207.

Hayashi, Masaki et al, Prostaglandin Analogues Possessing Antinidatory Effects. 1. Modification of the ω Chain, J. Med. Chem., 1980, 519-524, 23.

Hecker, Markus et al, Studies on the Interaction of Minoxidil with Prostacyclin Synthase in Vitro, Biochemical Pharmacology, 1988, 3363-3365, 37(17).

Hellberg, Mark et al, The Hydrolysis of the Prostaglandin Analog Prodrug Bimatoprost to 17-Phenyltrinor PGF2α by Human and Rabbit Ocular Tissue, J. Ocular Pharmacol. Ther., 2003, 97-103, 19(2).

Higginbotham, Eve et al, One-Year, Randomized Study Comparing Bimatoprost and Timolol in Glaucoma and Ocular Hypertension, Archives of Opthalmology, Oct. 2002, 1286-1293, 120 (10), US.

Houssay, Alerto, Effects of Prostaglandins Upon Hair Growth in Mice, Acta Physiol. Latinoam., 1976, 186-191, 26.

Huang, A. et al, Different Modes of Inhibition of Increase in Cytosolic Calcium and Aggregation of Rabbit Platelets by Two Thromboxane A2 Antagonists, Asia Pacific Journal of Pharmacology, 1994, 163-171, 9.

Hulan, H.W. et al, The Development of Dermal Lesions and Alopecia in Male Rats Fed Rapeseed Oil, Canadian Journal of Physiology and Pharmacology, 1976, 1-6, 54(1).

Hulan, H.W. et al, The Effect of Long-Chain Monoenes on Prostaglandin E2 Synthesis by Rat Skin, Lipids, 1977, 604-609, 12(7).

Ichikawa, A. et al, Molecular Aspects of the Structures and Functions of the Prostaglandin E Receptors, J. Lipid Mediators Cell Signalling, 1996, 83-87, 14.

Informa UK Ltd., AGN-192024, 2006, 3 Pages.

Inoue, Hironishi, Thromboxane A2 receptor antagonists, Oct. 1996, 1221-1225, 32(10), Pharmaceutical Society of Japan.

J Am Pharm Assoc-, Agents for Glaucoma, New Drugs of 2001, 2001, 4 pages, 42(2), Journal of the American Pharmaceutical Association, http://www.edscape.com/viewarticle/436631_22, US.

(56) References Cited

OTHER PUBLICATIONS

Jakobsson, Per-Johan et al, Membrane-Associated Proteins in Eicosanoid and Glutathione Metabolism (MAPEG), American Journal of Respiratory and Critical Care Medicine, 2000, S20-S24, 161.
Jimenez, J.J. et al, Stimulated Monocyte-Conditioned Media Protect From Cytosine Arabinoside-Induced Alopecia in Rat, Friday Afternoon Subspecialty Meetings, 1990, 973A.
Johnstone, M.A., Brief Latanoprost RX Induces Hypertrichosis, Glaucoma Clinical Pharmacology II Poster Presentation, 1998, S258, 39(4).
Johnstone, Murray et al, Prostaglandin-Induced Hair Growth, Survey of Ophthalmology, Aug. 2002, S185-S202, 47(Suppl 1).
Johnstone, Murray, Hypertrichosis and Increased Pigmentation of Eyelashes and Adjacent Hair in the Region of the Ipsilateral Eyelids of Patients Treated With Unilateral Topical Latanoprost, American Journal of Ophthalmology, 1997, 544-547, 124(4).
Jordan, B.A. et al, G-Protein-Coupled Receptor Heterodimerization Modulates Receptor Function, Nature, Jun. 17, 1999, 697-700, 399(6737).
Karim, S.M. et al, Prostaglandins and Human Respiratory Tract Smooth Muscle: Structure Activity Relationship, Advances in Prostaglandin and Thromboxane Research, 1980, 969-980, 7.
Krauss, Achim et al, Evidence for Human Thromboxane Receptor Heterogeneity Using a Novel Series of 9,11-Cyclic Carbonate Derivatives of Prostaglandin F2α, British Journal of Pharmacology, 1996, 1171-1180, 117.
Katz, L.J. et al, Comparison of Human Ocular Distribution of Bimatoprost and Latanoprost, 2010, P450.
Kaufman, Paul, Effects of Intracamerally Infused Prostaglandins on Outflow Facility in Cynomolgus Monkey Eyes with Intact or Retrodisplaced Ciliary Muscle, Experimental Eye Research, 1986, 819-827, 43.
Kende, Andrew et al, Prostaglandin Phosphonic Acids Through Homolytic Halodecarboxylation of Prostaglandins F1α and F2α, Tetrahedron Letters, 1999, 8189-8192, 40.
Kerstetter, J.R. et al, Prostaglandin F2α-1-Isopropylester Lowers Intraocular Pressure Without Decreasing Aqueous Humor Flow, American Journal of Ophthalmology, 1988, 30-34, 105.
Kiriyama, Michitaka et al, Ligand Binding Specificities of the Eight Types and Subtypes of the Mouse Prostanoid Receptors Expressed in Chinese Hamster Ovary Cells, British Journal of Pharmacology, 1997, 217-224, 122.
Kluender, Harold et al, The Synthesis of Dimethylphosphonoprostaglandin Analogs, Prostaglandins and Medicine, 1979, 441-444, 2.
Kreilgaard, Mads, Influence of Microemulsions on Cutaneous Drug Delivery, Advanced Drug Delivery Reviews, 2002, S77-S98, 54 Suppl. 1.
Kvedar, Joseph et al, Topical Minoxidil in the Treatment of Male Pattern Alopecia, Pharmacotherapy, 1987, 191-197, 7(6).
Lachgar, S. et al, Effect of VEGF and Minoxidil on the Production of Arachidonic Acid Metabolites by Cultured Hair, Dermal Papilla Cells, Eur. J. Dermatol., 1996, 365-368, 6.
Lachgar, S. et al, Hair Dermal Papilla Cell Metabolism is Influenced by Minoxidil, Fundamental & Clinical Pharmacology, 1997, 178, 11(2).
Lachgar, S. et al, Modulation by Minoxidil and VEGF of the Production of Inflammatory Mediators by Hair Follicle Dermal Papilla Cells, Groupe de Rocherche Dermatologique, 1995, 161, 104(1).
Lambert, Joseph, Clinical Study Report, A Multicenter, Double-Masked, Randomized, Parallel, 3-Month study (with Treatment Extended to 1 year) of the Safety and Efficacy of AGN 192024 0.03% Ophthalmic Solution Administered Once-Daily or Twice-daily Compared with Timolol 0.5% Ophthalmic Solution Administered Twice-Daily in Subjects with Glaucoma or Ocular Hypertension, Study No. 192024-009, Phase 3, 1998.
Lardy, C. et al, Antiaggregant and Antivasospastic Properties of the New Thromboxane A2 Receptor Antagonist Sodium 4-[[1-[[[(4 Chlorophenyl)sulfony]amino]methyl]cyclopentyl]methyl] enzeneacetate, Arzneim.-Forsch./Drug Res., 1994, 1196-1202, 44(11).

Lee, Ping-Yu et al, The Effect of Prostaglandin F2α on Intraocular Pressure in Mormotensive Human Subjects, Investigative Ophthalmology & Visual Science, Oct. 1988, 1474-1477, 29(10).
Lee, Vincent et al, Improved Ocular Drug Delivery with Prodrugs, Prodrugs: Topical and Ocular Drug Delivery, 1992, 221-297, Kenneth Sloan Edition.
Liang, Y. et al, Identification and Pharmacological Characterization of the Prostaglandin FP Receptor and FP Receptor Variant Complexes, Br. J. Pharmacol., 2008, 1079-1093, 154.
Liljebris, Charlotta et al, Derivatives of 17-Phenyl-18,19,20-trinorprostaglandin F2α Isopropyl Ester: Potential Antiglaucoma Agents, J. Med. Chem., 1995, 289-304, 38.
Ling, Geng et al, 16,16 dm Prostaglandin E2 Protects Mice From Fractionated Radiation-Induced Alopecia, Clinical Research, 1990, 858A, 38(3).
Lumigan 6-Month Phase 3 Data Presented at American Glaucoma Society Meeting, Mar. 2, 2001, 4 pages, Business Wire.
Lumigan Package Insert, Mar. 2001, 6 Pages, NDA 21-275.
Lundy, M.W. et al, Restoration of Cancellous Architecture and Increased Bone Strength in Aged Osteopenic Rats Treated with Fluprostenol, 21st Annual Meeting of the American Society for Bone and Mineral Research, 1999, S401.
Maddox, Yvonne et al, Amide and I-amino Derivatives of F Prostaglandins as Prostaglandin Antagonists, Nature, Jun. 15, 1978, 549-552, 273.
Malkinson, Frederick et al, Prostaglandins Protect Against Murine Hair Injury Produced by Ionizing Radiation of Doxorubicin, J. Invest Dermatol., 1993, 135S-137S, 101.
Mansberger, Steven et al, Eyelash Formation Secondary to Latanoprost Treatment in a Patient With Alopecia, Arch. Opthalmol., 2000, 718-719, 118.
Maruyama, Takayuki et al, EP1 Receptor Antagonists Suppress Tactile Allodynia in Rats, Prostaglandins & Other Lipid Mediators, 1999, 217(Abstract), 59.
Matsumura, H. et al, Brain and Neuroscience, 1998, 79-89.
Maurer, Marcus et al, Hair Growth Modulation by Topical Immunophilin Ligands, American Journal of Pathology, Apr. 1997, 1433-1441, 150(4).
Maw, Graham, Chapter 8. Pharmacological Therapy for the Treatment of Erectile Dysfunction, Annual Reports in Medicinal Chemistry, 1999, 71-80.
Maxey, Kirk, The Hydrolysis of Bimatoprost in Corneal Tissue Generates a Potent Prostanoid FP Receptor Agonist, Survey of Ophthalmology, Aug. 2002, S34-S40, 47 (Supp. 1).
McCullough, Peter et al, Ridogrel Janssen, Current Opinion in Antiinflammatory & Immunodulatory Investigational Drugs, 1999, 265-276, 1(3).
McMurry, John, Amides, Organic Chemistry, 1984, 794.
Medical Review, Application No. 21-275, Center for Drug Evaluation and Research, 2001.
Medline, Bimatoprost (Ophthalmic), Bimatoprost, Jul. 24, 2001, 4 pages, Medlineplus. Health Information, Online.
Michelet, Jean-Francois et al, Activation of Cytoprotective Prostaglandin Synthase-1 by Minoxidil as a Possible Explanation for Its Hair Growth-Stimulating Effect, J. Invest Dermatol., 1997, 205-209, 108.
Mihele, Densia et al, Cercetarea Actiunii Hepatoprotectoare A Unor Prostaglandine De Sinteza, Farmacia, 1999, 43-58, 67(5).
Millikan, Larry, Treatment of Alopecia, The Journal of Clinical Pharmacology, 1987, 715, 27(8).
Millikan, Larry, Treatment of Male Pattern Baldness, Drug Therapy, 1989, 62-73.
Mishima, Hiromu, A Comparison of Latanoprost and Timolol in Primary Open-Angle Glaucoma and Ocular Hypertension, Arch. Opthalmol., 1996, 929-932, 114.
Miyamoto, Terumasa et al, A Comparison in the Efficacy and Safety Between Ramatroban (BAY u 3405) and Ozagrel-HCl for Bronchial Asthma—A Phase III, Multi-Center, Randomized, Double-Blind, Group Comparative Study, 1997, 599-639.
Mori, S. et al, Effects of Prostaglandin E2 on Production of New Cancellous Bone in the Axial Skeleton of Ovariectomized Rats, Bone, 1990, 103-113, 11.

(56) References Cited

OTHER PUBLICATIONS

Muller-Rover, Sven et al, A Comprehensive Guide for the Accurate Classification of Murine Hair Follicles in Distinct Hair Cycle Stages, J. Invest Dermatol, 2001, 3-15, 117.

Mura, Simona et al, Penetration Enhancer-Containing Vesicles (PEVs) as Carriers for Cutaneous Delivery of Minoxidil, International Journal of Pharmaceutics, 2009, 72-79, 380.

Murakami, T. et al, Effect of Isocarbacyclin Methyl Ester Incorporated in Lipid Microspheres on Experimental Models of Peripheral Obstructive Disease, Drug Res., 1995, 991-994, 45(9).

Narumiya, Shuh et al, Roles of Prostanoids in Health and Disease; Lessons From Receptor-Knockout Mice, Common Disease: Genetic and Pathogenetic Aspects of Multifactorial Diseases, 1999, 261-269.

Neau, Steven, Pharmaceutical Salts, Water-Insoluble Drug Formulation, 2008, 417-435.

Negishi, Manabu et al, Molecular Mechanisms of Diverse Actions of Prostanoid Receptors, Biochimica et Biophysica Acta, 1995, 109-120, 1259.

New Drugs for Glaucoma, FDA Consumer Magazine, May-Jun. 2001.

Norrdin, R.W. et al, The Role of Prostaglandins in Bone in Vivo, Prostaglandins Leukotrienes and Essential Fatty Acids, 1990, 139-149, 41.

Olsen, Elise et al, Transdermal Viprostol in the Treatment of Male Pattern Baldness, J. Am. Acad. Dermatol., 1990, 470-472, 23.

Orlicky, D.J., Negative Regulatory Activity of a Prostaglandin F2α Receptor Associated Protein (FPRP), Prostaglandins, Leukotrienes and Essential Fatty Acids, 1996, 247-259, 54(4).

Ortonne, Jean-Paul et al, Hair Melanin's Hair Color: Ultrastructural and Biochemical Aspects, Journal of the Society for Investigative Dermatology, 1993, 82S-89S.

Paragraph IV Letter, Jul. 26, 2010.

Paus, Ralf et al, The Induction of Anagen Hair Growth in Telogen Mouse Skin by Cyclosporine A Administration, Laboratory Investigation, 1989, 365-369, 60(3).

Pfeiffer, N, New Developments in Glaucoma Drug Therapy, Ophthalmologist, 1992, W1-W13, 89.

Pharmaprojects No. 6321, 2006, 1 page.

Phase 3 Lumigan—AGN 192024—Data Presented at American Academy of Ophthalmology, Allergan Press Release, Mar. 1, 2000.

Physicians' Desk Reference, 56th ed., pp. 212-213, 543, 553-554, 2864-2865 (2002).

Poyer, J.F. et al, Prostaglandin F2α Effects on Isolated Rhesus Monkey Ciliary Muscle, Invest. Ophthalmol. Vis. Sci., Nov. 1995, 2461-2465, 36(12).

Preparation of '404 Patent Documents for European Patent Office; Defendant Athena Cosmetics, Inc., Supplemental Invalidity Contentions Pursuant to Patent Local Rule 3-3, 2009.

Preparation of '404 Patent Documents for European Patent Office; Defendant Peter Thomas Roth Labs LLC and Peter Thomas Roth, Inc.'s Invalidity Contentions Pursuant to Patent Local Rule 3-3, 2009.

Preparation of '404 Patent Documents for European Patent Office; Defendants Metrics LLC, Product Innovations LLC; Stella International LLC; and Nutra-Luxe, M.D. LLC's; Local Patent Rule 3-3 Preliminary Invalidity Contentions, 2009.

Preparation of '404 Patent Documents for European Patent Office; Invalidity Contentions Pursuant to Patent Local Rule 3-3, 2008.

Rampton, D.S. et al, Anti-inflammatory Profile in Vitro of Ridogrel, A Putative New Treatment for Inflammatory Bowel Disease, Immunology, Microbiology, and Inflammatory Disorders, 1999, G3477.

Resul, B et al, Phenyl-substituted Prostaglandins: Potent and Selective Antiglaucoma Agents, J. Med. Chem., Jan. 22, 1993, 243-248, 36(2).

Reynolds, A, Darkening of Eyelashes in a Patient Treated With Latanoprost, Eye, 1998, 741-743, 12.

Rigaudy, J. et al, Nomenclature of Organic Chemistry Sections A, B. C, D, E, F, and H, InCL Union of Pure & Applied Chemistry, Organic Chemistry Div., Comm'n on Nomenclature of Organic Chemistry, 1979, 255-256.

Roenigk, Henry, New Topical Agents for Hair Growth, Clinics in Dermatology, 1988, 119-121, 6(4).

Romano, Maria Rosaria et al, Evidence for the Involvement of Cannabinoid DB1 Receptors in the Bimatoprost-Induced Contractions on the Human Isolated Ciliary Muscle, Investigative Ophthalmology & Visual Science, Aug. 2007, 3677-3382, 48(8).

Roof, S.L. et al, mRNA Expression of Prostaglandin Receptors EP1, EP2, EP3 and EP4 in Human Osteoblast-Like Cells and 23 Human Tissues, 18 Annual Meeting of the American Society for Bone and Mineral Research, 1996, S337.

Roseborough, Ingrid et al, Lack of Efficacy of Topical Latanoprost and Bimatoprost Ophthalmic Solutions in Promoting Eyelash Growth in Patients with Alopecia Areata, J Am Acad Dermtol, Apr. 2009, 705-706, 60(4).

Ruel, Rejean et al, New Class of Biphenylene Dibenzazocinones as Potent Ligands for the Human EP1 Prostanoid Receptor, Bioorganic & Medicinal Chemistry Letters, 1999, 2699-2704, 9.

Saeki, Hideshisa et al, Guidelines for Management of Atopic Dermatitis, Journal of Dermatology, 2009, 563-577, 36.

Sakuma, Yoko et al, Crucial Involvement of the EP4 Subtype of Prostaglandin E Receptor in Osteoclast Formation by Proinflammatory Cytokines and Lipopolysacharide, Journal of Bone and Mineral Research, 2000, 218-227, 15(2).

Sauk, John et al, Influence of Prostaglandins E1, E2, and Arachidonate on Melanosomes in Melanocytes and Keratinocytes of Anagen Hair Bulbs in Vitro, The Journal of Investigative Dermatology, 1975, 332-337, 64.

Scheider, Marlon et al, The Hair Follicle as a Dynamic Miniorgan, Current Biology, 2009, R132-R142, 19.

Sharif, N.A. et al, [3H]AL-5848 ([3H]9β-(+)-Fluprostenol). Carboxylic Acid of Travoprost (AL-6221), a Novel FP Prostaglandin o Study the Pharmacology and Autoradiographic Localization of the FP Receptor, J. Pharm. Pharmacol., 1999, 685-694, 51.

Sharif, N.A. et al, Cat Iris Sphincter Smooth-Muscle Contraction: Comparison of FP-Class Prostaglandin Analog Agonist Activities, J. Ocul. Pharmacol. Ther., Apr. 2008, 152-163, 24(2).

Sharif, N.A. et al, Human Ciliary Muscle Cell Responses to FP-class Prostaglandin Analogs: Phosphoinositide Hydrolysis, Intracellular Ca2+ Mobilization and MAP Kinase Activation, J. Ocul. Pharmacol Ther., 2003, 437-455, 19.

Sharif, N.A. et al, Human Trabecular Meshwork cell Responses Induced by Bimatoprost, Travoprost, Unoprostone, and Other FP Prostaglandin Receptor Agonist Analogues, Invest. Ophthalmol Vis. Sci., 2003, 715-721, 44.

Sharif, N.A. et al, Ocular Hypotensive FP Prostaglandin (PG) Analogs: PG Receptor Subtype Binding Affinities and Selectivities, and Agonist Potencies at FP and Other PG Receptors in Cultured Cells, Journal of Ocular Pharmacology and Therapeutics, 2003, 501-515, 19(6).

Sharif, N.A. et al, Update and Commentary on the Pro-Drug Bimatoprost and a Putative Prostamide Receptor, Expert Rev. Ophthalmol., 2009, 477-489, 4(5).

Sharif, Najam, Bimatoprost and Its Free Acid Are Prostaglandin FP Receptor Agonists, European Journal of Pharmacology, 2001, 211-213, 432.

Sherwood, Mark et al, Six-Month Comparison of Bimatoprost Once-Daily and Twice-Daily with Timolol Twice-Daily in Patients with Elevated Intraocular Pressure, Survey of Ophthalmology, 2001, S361-S368, 45(4).

Shih, Mei-Shu et al, PGE2 Induces Regional Remodeling Changes in Haversian Envelope: a Histomorphometric Study of Fractured Ribs in Beagles, Bone and Mineral, 1986, 227-264, 1.

Shimazaki, Atsushi et al, Effects of the New Ethacrynic Acid Derivative SA9000 on Intraocular Pressure in Cats and Monkeys, Biol. Pharm. Bull., 2004, 1019-1024, 27(7).

Shimazaki, Atsushi et al, New Ethacrynic Acid Derivatives as Potent Cytoskeletal Modulators in Trabecular Meshwork Cells, Bio. Pharm. Bull., 2004, 846-850, 27(6).

Sjoquist, Birgitta et al, Ocular and Systemic Pharmacokinetics of Latanoprost in Humans, Surv. Ophthalmol., Aug. 2002, S6-S12, 47(Suppl 1).

Sjoquist, Birgitta et al, Pharmacokinetics of Latanoprost in the Cynomolgus Monkey. 3rd Communication: Tissue Distribution After

(56) References Cited

OTHER PUBLICATIONS

Topical Administration on the Eye Studied by Whole Body Autoradiography, Glaucoma Research Laboratories. Arzneim-Forsch/Drug Res., 1999, 240-249, 49.

Sorbera, L.A. et al, Travoprost, Drugs of the Future, 2000, 41-45, 25(1).

Souillac, Pierre et al, Characterization of Delivery Systems, Differential Scanning Calorimetry, 1999, 212-227, 49.

Spada, C.S. et al, Bimatoprost and Prostaglandin F2α Selectively Stimulate Intracellular Calcium Signaling in Different Cat iris Sphincter Cells, Exp. Eye Res., Jan. 2005, 135-145, 80(1).

Sredni, Benjamin et al, The Protective Role of the Immunomodulator AS101 Against Chemotherapy-Induced Alopecia Studies on Human and Animal Models, Int. J. Cancer, 1996, 97-103, 65.

Stahl, Heinrich et al, Chapter 12: Monographs on Acids and Bases, Handbook of Pharmaceutical Salts, 2008, 265-327.

Stamer, W.D. et al, Cellular Basis for Bimatoprost Effects on Human Conventional Outflow, Invest. Ophthalmol. Vis. Sci., Oct. 2010, 5176-5181, 51(10).

Stjernschantz, Johan et al, From PGF2α-isopropyl Ester to Latanoprost: A Review of the Development of Xalatan: The Proctor Lecture, Invest. Ophthalmol. Vis. Sci., May 2001, 1134-1145, 42(6).

Stjernschantz, Johan et al, Phenyl Substituted Prostaglandin Analogs for Glaucoma Treatment, Phenyl Substituted Prostaglandin Analogs for Glaucoma Treatment, 1992, 691-704, 17(8).

Stjernschantz, Johan et al, Studies on Ocular Inflammation and Development of a Prostaglandin Analogue for Glaucoma Treatment, Exp. Eye Res., Apr. 2004, 759-766, 78(4).

Supplement A (Lumigan®), Physician's Desk Reference 2001, Mar. 2001.

Swarbrick, James et al, Salt Forms of Drugs and Absorption, Encyclopedia of Pharmaceutical Technology, 1988, 453-499, 13.

Terada, Nobuhisa et al, Effect of a Thromboxane A2 Receptor Antagonist Ramatroban (BAY u 3405), on Inflammatory Cells, Chemical Mediators and Non-Specific Nasal Hyperreactivity After Allergen Challenge in Patients with Perennial Allergic Rhinitis, Allergoloy International, 1998, 59-67, 47.

The Newsletter of Glaucoma Foundation, 2000, 11 pages, 11(2).

Titus, Reuben, Aloe Vera—The Magical Plant Amongst Us, 2009, 12 Pages, http://www.scribd.com/doc/19139862/Aloe-VeraMiracle-Plant.

Tobin, Desmond, Aging of the Hair Follicle Pigmentation System, Int. J. Trichology, Jul.-Dec. 2009, 83-93, 1(2).

Tomita, Yasushi et al, Melanocyte-Stimulating Properties of Arachidonic Acid Metabolites: Possible Role in Postinflammatory Pigmentation, Pigment Cell Research, 1992, 357-361, 5.

Topical Emu Oil and Coconut Oil for Hair Loss—A Potent Combination, 2010, 3 Pages, www.hairloss-research.org/blog/?p=15.

Tosti, Antonella et al, Hypertrichosis of the Eyelashes Caused by Bimatoprost, J Am Acad Dermatol, Nov. 2004, S149-S150, 51(5).

Travatan (travoprost ophthalmic solution) 0.004% Product Insert, NDA 21-257, Mar. 16, 2001, 7 Pages.

U.S. Appl. No. 11/805,122, Resp. to Office Action dated Jan. 21, 2009.

Ueda, Ken et al, Cortical Hyperostosis Following Long-Term Administration of Prostaglandin E1 in Infants with Cyanotic Congenital Heart Disease, Journal of Pediatrics, 1980, 834-836, 97(5).

United States Court of Appeals for the Federal Circuit, *Allergan, Inc., and Duke University v. Apotex Inc., Apotex Corp., Sandoz, Inc., and Hi-Tech Pharmacal Co., Inc.*, 2014, 41 Pages.

Uno, Hideo et al, Effect of Latanoprost on Hair Growth in the Bald Scalp of the Stump-Tailed Macacque: A Pilot Study, Acta Derm Venereol, 2002, 7-12, 82.

Van Alphen, G.W.H.M. et al, The effect of Prostaglandins on the Isolated Internal Muscles of the Mammalian Eye, Including Man, Documenta Ophthalmologica, 1977, 397-415, 42(4).

Vandenburg, A.M. et al, A One-Month Dose Response Study of AGN 192024, A Novel Antiglaucoma Agent, in Patients with Elevated Intraocular Pressure, Glaucoma Clinical Pharmacology IV Poster Presentation, 1999, S830, 40(4).

Vandenburgh, Amanda, reply to Alan L. Robin, An Accurate Comparison of Bimatoprost's Efficacy and Adverse Effects, Arch Ophthalmol, Jul. 2002, 997-1000, 120.

Vayssairat, Michael, Preventive Effect of an Oral prostacyclin Analog, Beraprost Sodium, on Digital Necrosis in Systemic Sclerosis, J. Rheumatol, 1999, 2173-2178, 26.

Vengerovsky, A.I. et al, Hepatoprotective action of prostaglandins, Experimental and Clinical Pharmacology, 1997, 78-82, 60(5).

Verbeuren, T. et al, The TP-Receptor Antagonist S 18886 Unmasks Vascular Relaxation and Potentiates the Anti-Platelet Action of PGD2, New Antithrombotic Agents, Jun. 11, 1997, 693.

Verma, DD et al, Treatment of Alopecia Areata in the DEBR Model Using Cyclosporin A Lipid Vesicles, Eur. J. Dermatol, 2004, 332-338, 14.

Vielhauer, G.A. et al, Cloning and Localization of hFP(S): a Six-Transmembrane mRNA Splice Variant of the Human FP Prostanoid Receptor, Arch Biochem Biophys., Jan. 15, 2004, 175-185, 421(2).

Villumsen, J. et al, Prostaglandin F2α-isopropylester Eye Drops: Effect on Intraocular Pressure in Open-Angle Glaucoma, Br. J. Ophthalmol., 1989, 975-979, 73.

Vincent, J.E. et al, Letter to the Editor Prostaglandin Synthesis and Selenium Deficiency a Hypothesis, Prostaglandins, 1974, 339-340, 8(4).

Vippagunta, Sudha et al, Crystalline Solids, Advanced Drug Delivery Reviews, 2001, 3-26, 48.

Voss, N.G. et al, Induction of Anagen Hair Growth in Telogen Mouse Skin by Topical Latanoprost Application, Glaucoma Pharmacology, Cellular, Mechanism II, Mar. 15, 1999, S676, 40(4).

Waddell, K.A. et al, Combined Capillary Column Gas Chromatography Negative Ion Chemical Ionization Mass Spectrometry of Prostanoids, Biomedical Mass Spectrometry, 1983, 83-88, 10(2).

Wand, Martin, Latanoprost and Hyperpigmentation of Eyelashes, Arch Ophthalmology, Sep. 1997, 1206-1208, 115.

Wang, Yili et al, Design and Synthesis of 13,14-Dihydro Prostaglandin F1α Analogues as Potent and Selective Ligands for the Human FP Receptor, J. Med. Chem., 2000, 945-952, 43.

Watson, Peter et al, A Six-month, Randomized, Double-masked Study Comparing Latanoprost with Timolol in Open-Angle Glaucoma and Ocular Hypertension, Ophthalmology, 1996, 126-137, 103.

Whitcup, Clinical Study Report, A Multi-Center, Investigator-Marked, Randomized, Parallel Study of the Safety and Efficacy of AGN 192024 0.03% Ophthalmic Solution Compared with Latanoprost 0.005% Ophthalmic Solution Administered Once-Daily in Subjects with Glaucoma or Ocular Hypertension, Study No. 192024-010-01, Phase 3b, 1999.

White, J.H. et al, Heterodimerization is Required for the Formation of a Functional GABA(B) Receptor, Nature, Dec. 17, 1998, 679-682, 396(6712).

Whitson, Jess, Travoprost—a New Prostaglandin Analogue for the Treatment of Glaucoma, Expert Opin. Pharmacother, 2002, 965-977, 3 (7).

Willis, Anthony, Prostaglandins and Related Lipids, vol. I, Chemical and Biochemical Aspects, CRC Handbook of Eicosanoids, 1987, 80-97, 1.

Wilson, S.J. et al, Dimerization of the Human Receptors for Prostacyclin and Thromboxane Facilitates Thromboxane Receptor-Mediated CAMP Generation, J. Biol. Chem., Dec. 17, 2004, 53036-53047, 279(51).

Woodward, David et al, Bimatoprost Effects on Aqueous Humor Dynamics in Monkeys, J. Ophthalmol., 2010, 1-5, vol. 2010.

Woodward, David et al, Bimatoprost: a Novel Antiglaucoma Agent, Cardiovascular Drug Reviews, 2004, 103-120, 22(2).

Woodward, David et al, Emerging Evidence for Additional Prostanoid Receptor Subtypes, Current Topics in Pharmacology, 1998, 153-162, 4.

Woodward, David et al, Identification of an antagonist that selectively blocks the activity of prostamides (prostaglandin-ethanolamides) in the feline iris, British Journal of Pharmacology, 2007, 342-352, 150.

Woodward, David et al, Molecular Characterization and Ocular Hypotensive Properties of the Prostanoid EP2 Receptor, Journal of Ocular Pharmacology, 1995, 447-454, 11(3).

(56) References Cited

OTHER PUBLICATIONS

Woodward, David et al, Prostaglandin F2α (PGF2α) 1-Ethanolamide: A Unique Local Hormone Biosynthesized From Anandamide, 11th Intl Conf. Advances Prostaglandin & Leukotriene Res.: Basic Sci. & New Clinical Applications—Abstract Book 27, 2000, 1 page.

Woodward, David et al, Replacement of Carboxylic Acid Group of Prostaglandin F2α with a Hydroxyl or Methoxy Substituent Provides Biologically Unique Compounds, British Journal of Pharmacology, Aug. 2000, 1933-1943, 130(8).

Woodward, David et al, Studies on the Ocular Effects of Pharmalogically Novel Agent Prostaglandin F2α 1-OCH3 (AGN 191129), Eicosanoids, 1998, R719.

Woodward, David et al, The Pharmacology of Bimatoprost (LumiganTM), Sury Ophthalmol, 2001, S337-S345, Suppl 4.

Woodward, David, Pharmacological Characterization of a Novel Antiglaucoma Agent, Bimatoprost (AGN 192024), J. Pharmacol. Exp. Ther., Jan. 24, 2003, 772-785, 305 (2).

Xalatan (Latanoprost Ophthalmic Solution) 0.005% Product Insert, 2001, 4 Pages.

Xalatan® Eye Drops, Retrieval Date : Oct. 2, 2010, 3 pages, http://home.intekom.com/pharm/pharmaca/xalatan.html.

Yamaji, K. et al, Prostaglandins E1 and E2, but not F2α or Latanoprost, Inhibit Monkey Ciliary Muscle Contraction, Curr. Eye Res., Aug. 2005, 661-665, 30(8).

Zeigler, Tania, Old Drug New Use: New Research Shows Common Cholesterol-Lowering Drug Reduces Multiple Sclerosis Symptoms in Mice, National Institute of Neurological Disorders and Stroke, Jan. 6, 2003, 2 Pages.

Zimbric, M.L. et al, Effects of Latanoprost of Hair Growth in the Bald Scalp of Stumptailed Macaques, Glaucoma Pharmacology, Cellular Mechanism II, 1999, 3569-B427—Abstract, vol. 40, No. 4.

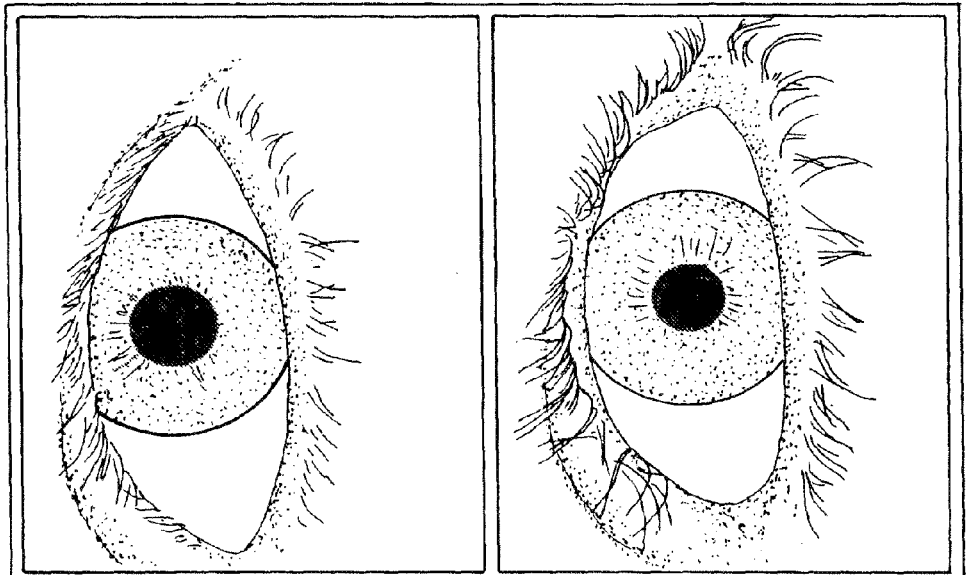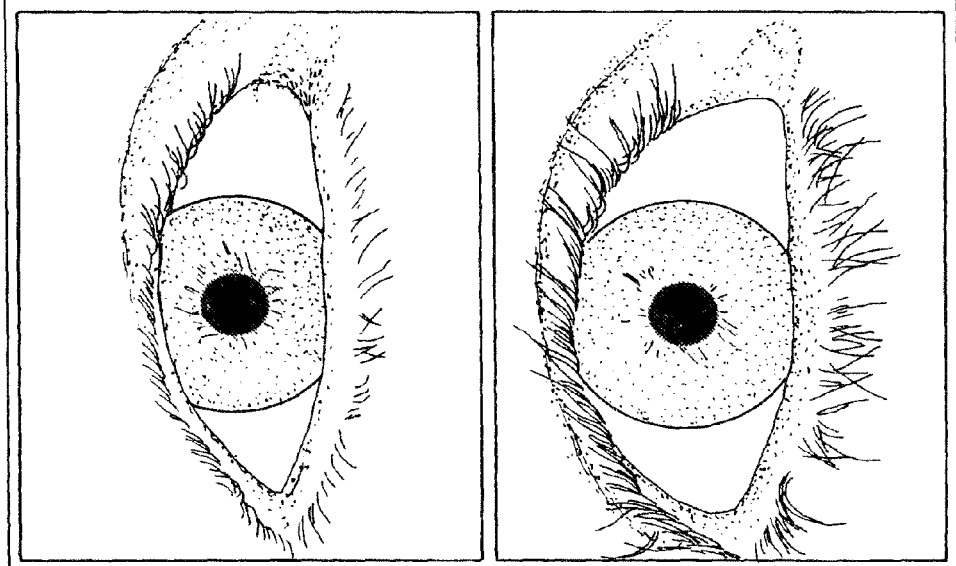

METHOD OF ENHANCING HAIR GROWTH

RELATED APPLICATIONS

This patent application is a continuation of U.S. patent application Ser. No. 13/937,512, filed Jul. 9, 2013, which is a continuation of U.S. patent application Ser. No. 13/441,783, filed Apr. 6, 2012, now U.S. Pat. No. 8,632,760, issued Jan. 21, 2014, which is a continuation of U.S. patent application Ser. No. 13/356,284, filed Jan. 23, 2012, now U.S. Pat. No. 8,263,054, issued Sep. 11, 2011, which is a continuation of U.S. patent application Ser. No. 12/425,933, filed Apr. 17, 2009, now U.S. Pat. No. 8,298,518, issued Oct. 30, 2012, which is a continuation of U.S. patent application Ser. No. 11/943,714, filed Nov. 21, 2007, now U.S. Pat. No. 8,038,988, issued Oct. 18, 2011, which is a continuation of U.S. patent application Ser. No. 11/805,122, filed May 22, 2007, now U.S. Pat. No. 8,101,161, issued Jan. 24, 2012, which is a continuation of U.S. patent application Ser. No. 10/345,788, which was filed on Jan. 15, 2003, now U.S. Pat. No. 7,351,404, issued Apr. 1, 2008, which claims the benefit of U.S. Provisional Application No. 60/354,425, filed on Feb. 4, 2002, all of which are hereby incorporated by reference herein.

FIELD OF THE INVENTION

This invention relates to a method for stimulating the growth of mammalian hair comprising the application to mammalian skin of a cyclopentane heptanoic acid, 2-cycloalkyl or arylalkyl derivative or a pharmacologically acceptable acid addition salt thereof, alone, or in association with a topical pharmaceutical carrier.

BACKGROUND OF THE INVENTION

Dermatologists recognize many different types of hair loss, the most common by far being "alopecia" wherein human males begin losing scalp hair at the temples and on the crown of the head as they get older. While this type of hair loss is largely confined to males, hence its common name "male pattern baldness," it is not unknown in women. No known cure has yet been found despite continuing attempts to discover one.

A good deal is known about various types of human hair and its growth patterns on various parts of the body.

For purposes of the present invention, it is necessary to consider various types of hair, including, terminal hairs and vellus hairs and modified terminal hairs, such as seen in eye lashes and eye brows. Terminal hairs are coarse, pigmented, long hairs in which the bulb of the hair follicle is seated deep in the dermis. Vellus hairs, on the other hand, are fine, thin, non-pigmented short hairs in which the hair bulb is located superficially in the dermis. As alopecia progresses, a transition takes place in the area of approaching baldness wherein the hairs themselves are changing from the terminal to the vellus type.

Another factor that contributes to the end result is a change in the cycle of hair growth. All hair, both human and animal, passes through a life cycle that includes three phases, namely, the anagen phase, the catagen phase and the telogen phase. The anagen phase is the period of active hair growth and, insofar as scalp hair is concerned, this generally lasts from 3-5 years. The catagen phase is a short transitional phase between the anagen and telogen phases which, in the case of scalp hair, lasts only 1-2 weeks. The final phase is the telogen phase which, for all practical purposes, can be denominated a "resting phase" where all growth ceases and the hair eventually is shed preparatory to the follicle commencing to grow a new one. Scalp hair in the telogen phase is also relatively short-lived, some 3-4 months elapsing before the hair is shed and a new one begins to grow.

Under normal hair growth conditions on the scalp, approximately 88% of the hairs are in the anagen phase, only 1% in catagen and the remainder in telogen. With the onset of male pattern baldness, a successively greater proportion of the hairs are in the telogen phase with correspondingly fewer in the active growth anagen phase.

Alopecia is associated with the severe diminution of hair follicles. A bald human subject will average only about 306 follicles per square centimeter, whereas, a non-bald human in the same age group will have an average of 460 follicles per square centimeter. This amounts to a one-third reduction in hair follicles which, when added to the increased proportion of vellus hair follicles and the increased number of hair follicles in the telogen phase, is both significant and noticeable. Approximately 50% of the hairs must be shed to produce visible thinning of scalp hair. It is thus a combination of these factors: transition of hairs from terminal to vellus, increased number of telogen hairs—some of which have been shed, and loss of hair follicles that produces "baldness".

While a good deal is known about the results of male pattern baldness, very little is known about its cause. The cause is generally believed to be genetic and hormonal in origin although, the known prior art attempts to control it through hormone adjustment have been singularly unsuccessful.

One known treatment for male pattern alopecia is hair transplantation. Plugs of skin containing hair are transplanted from areas of the scalp where hair is growing to bald areas with reasonable success; however, the procedure is a costly one in addition to being time-consuming and quite painful. Furthermore, the solution is inadequate from the standpoint that it becomes a practical, if not an economic, impossibility to replace but a tiny fraction of the hair present in a normal healthy head of hair.

Other non-drug related approaches to the problem include such things as ultra-violet radiation, massage, psychiatric treatment and exercise therapy. None of these, however, has been generally accepted as being effective. Even such things as revascularization surgery and acupuncture have shown little, if any, promise.

By far, the most common approach to the problem of discovering a remedy for hair loss and male pattern alopecia has been one of drug therapy. Many types of drugs ranging from vitamins to hormones have been tried and only recently has there been any indication whatsoever of even moderate success. For instance, it was felt for a long time that since an androgenic hormone was necessary for the development of male pattern baldness, that either systemic or topical application of an antiandrogenic hormone would provide the necessary inhibiting action to keep the baldness from occurring. The theory was promising but the results were uniformly disappointing.

The androgenic hormone testosterone was known, for example, to stimulate hair growth when applied topically to the deltoid area as well as when injected into the beard and pubic regions. Even oral administration was found to result in an increased hair growth in the beard and pubic areas as well as upon the trunk and extremities. While topical application to the arm causes increased hair growth, it is ineffective on the scalp and some thinning may even result. Heavy doses of testosterone have even been known to cause male pattern alopecia.

Certain therapeutic agents have been known to induce hair growth in extensive areas of the trunk, limbs and even occasionally on the face. Such hair is of intermediate status in that it is coarser than vellus but not as coarse as terminal hair. The hair is generally quite short with a length of 3 cm. being about maximum. Once the patient ceases taking the drug, the hair reverts to whatever is normal for the particular site after six months to a year has elapsed. An example of such a drug is diphenylhydantoin which is an anticonvulsant drug widely used to control epileptic seizures. Hypertrichosis is frequently observed in epileptic children some two or three months after starting the drug and first becomes noticeable on the extensor aspects of the limbs and later on the trunk and face. (The same pattern of hypertrichosis is sometimes caused by injury to the head.) As for the hair, it is often shed when the drug is discontinued but may, in some circumstances, remain.

Streptomycin is another drug that has been found to produce hypertrichosis, in much the same way as diphenylhydantoin, when administered to children suffering from tuberculous meningitis. About the same effects were observed and the onset and reversal of the hypertrichosis in relation to the period of treatment with the antibiotic leave little question but that it was the causative agent.

Two treatments have been demonstrated as showing some promise in reversing male pattern alopecia. These treatments include the use of a microemulsion cream containing both estradiol and oxandrolone as its active ingredients and the use of organic silicon.

In addition to the foregoing, it has been reported in U.S. Pat. Nos. 4,139,619 and 4,968,812 that the compound minoxidil is useful for the treatment of male pattern baldness. That compound, among others, has proven to have considerable therapeutic value in the treatment of severe hypertension. It is a so-called "vasodilator" which, as the name implies, functions to dilate the peripheral vascular system. Dermatologists and others have recognized that prolonged vasodilation of certain areas of the human body other than the scalp sometimes result in increased hair growth even in the absence of any vasodilating therapeutic agent. For instance, increased hair growth around surgical scars is not uncommon. Similarly, arteriovenous fistula have been known to result in increased vascularity accompanied by enhanced hair growth. Externally-induced vasodilation of the skin, such as, for example, by repeated biting of the limbs by the mentally retarded and localized stimulation of the shoulders by water carries has been known to bring on hypertrichosis in the affected areas. Be that as it may, similar techniques such as continued periodic massage of the scalp have been found to be totally ineffective as a means for restoring lost hair growth to the scalp. Scar tissue on the scalp inhibits rather than promotes hair growth.

U.S. Pat. No. 6,262,105 to Johnstone suggests that prostaglandins and derivatives thereof are useful in a method of enhancing hair growth.

Bimatoprost, which is sold by Allergan, Inc. of Irvine, Calif., U.S.A. as Lumigan® ophthalmic solution, for treating glaucoma now has been found as being effective to increase the growth of eyelashes when applied in the FDA approved manner.

It is, therefore, a principal object of the present invention to provide a novel and effective treatment for the stimulation of hair growth and the treatment of male pattern baldness.

Another object of the invention is to provide a method of stimulating hair growth in humans and non-human animals that is compatible with various types of therapeutic agents or carriers and, therefore, would appear to be combinable with those which, by themselves, demonstrate some therapeutic activity such as, for example, microemulsion creams or topical compositions containing estradiol and oxandrolone, minoxidil or agents that block the conversion of testosterone to dihydrotesterone (Procipia).

Still another objective is the provision of a treatment for the stimulation of hair growth which, while effective for its intended purpose, is apparently non-toxic and relatively free of unwanted side effects.

An additional object of the invention herein disclosed and claimed is to provide a method for treating hair loss in men or women which can be applied by the patient under medical supervision no more stringent than that demanded for other topically-administered therapeutic agents.

Other objects of the invention are to provide a treatment for male pattern alopecia which is safe, simple, painless, cosmetic in the sense of being invisible, easy to apply and quite inexpensive when compared with hair transplants and the like.

SUMMARY OF THE INVENTION

This invention provides pharmaceutical compositions for topical application to enhance hair growth comprising an effective amount of a cyclopentane heptanoic acid, 2-cycloalkyl or arylalkyl compound represented by the formula I

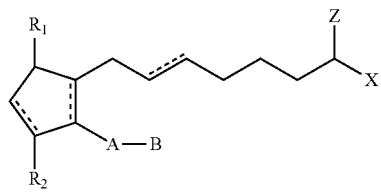

wherein the dashed bonds represent a single or double bond which can be in the cis or trans configuration, A is an alkylene or alkenylene radical having from two to six carbon atoms, which radical may be interrupted by one or more oxa radicals and substituted with one or more hydroxy, oxo, alkyloxy or alkylcarboxy groups wherein said alkyl radical comprises from one to six carbon atoms; B is a cycloalkyl radical having from three to seven carbon atoms, or an aryl radical, selected from the group consisting of hydrocarbyl aryl and heteroaryl radicals having from four to ten carbon atoms wherein the heteroatom is selected from the group consisting of nitrogen, oxygen and sulfur atoms; X is $-N(R^4)_2$ wherein $R^4$ is selected from the group consisting of hydrogen, a lower alkyl radical having from one to six carbon atoms,

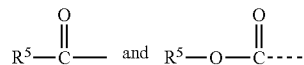

wherein $R^5$ is a lower alkyl radical having from one to six carbon atoms; Z is $=O$; one of $R_1$ and $R_2$ is $=O$, $-OH$ or a $-O(CO)R_6$ group, and the other one is $-OH$ or $-O(CO)R_6$, or $R_1$ is $=O$ and $R_2$ is H, wherein $R_6$ is a saturated or unsaturated acyclic hydrocarbon group having from 1 to about 20 carbon atoms, or $-(CH_2)mR_7$ wherein m is 0 or an integer of from 1 to 10, and $R_7$ is cycloalkyl radical, having from three to seven carbon atoms, or a hydrocarbyl aryl or heteroaryl radical, as defined above in free form or a pharmaceutically acceptable salt thereof, in association with a pharmaceutical carrier adapted for topical application to mammalian skin.

Preferably, the compound is a cyclopentane heptanoic acid, 2-(phenyl alkyl or phenyloxyalkyl) represented by the formula II

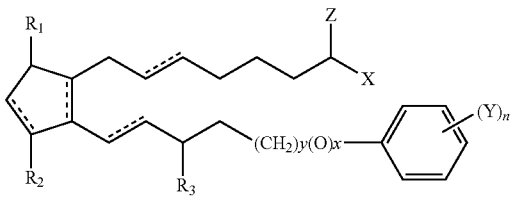

wherein y is 0 or 1, x is 0 or 1 and x and y are not both 1, Y is a radical selected from the group consisting of alkyl, halo, e.g. fluoro, chloro, etc., nitro, amino, thiol, hydroxy, alkyloxy, alkylcarboxy, halo substituted alkyl wherein said alkyl radical comprises from one to six carbon atoms, etc. and n is 0 or an integer of from 1 to 3 and $R_3$ is $=O$, $-OH$ or $-O(CO)R_6$ wherein $R_6$ is as defined above or a pharmaceutically acceptable salt thereof.

More preferably the compound is a compound of formula III.

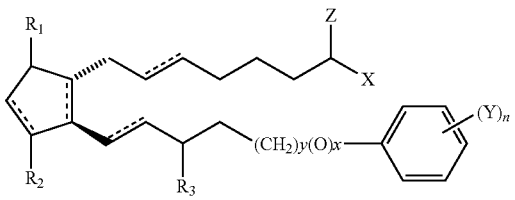

wherein hatched lines indicate α configuration, solid triangles are used to indicate β configuration.

More preferably y is 1 and x is O and $R_1$, $R_2$ and $R_3$ are hydroxy.

Most preferably the compound is cyclopentane N-ethyl heptanamide-5-cis-2-(3α-hydroxy-5-phenyl-1-trans-pentenyl)-3,5-dihydroxy, [$1_\alpha$,$2_\alpha$,$3_\alpha$,$5_\alpha$], also known as bimatoprost.

Another aspect of the invention provides methods for stimulating the rate of hair growth and for stimulating the conversion of vellus hair or intermediate hair to growth as terminal hair in a human or non-human animal by administering to the skin of the animal an effective amount of a compound wherein the compound has the formula:

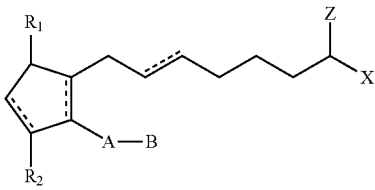

wherein the dashed bonds represent a single or double bond which can be in the cis or trans configuration, A is an alkylene or alkenylene radical having from two to six carbon atoms, which radical may be interrupted by one or more oxa radicals and substituted with one or more hydroxy, oxo, alkyloxy or alkylcarboxy groups wherein said alkyl radical comprises from one to six carbon atoms; B is a cycloalkyl radical having from three to seven carbon atoms, or an aryl radical, selected from the group consisting of hydrocarbyl aryl and heteroaryl radicals having from four to ten carbon atoms wherein the heteroatom is selected from the group consisting of nitrogen, oxygen and sulfur atoms; X is $-N(R^4)_2$ wherein $R^4$ is selected from the group consisting of hydrogen, a lower alkyl radical having from one to six carbon atoms,

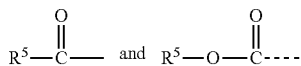

wherein $R^5$ is a lower alkyl radical having from one to six carbon atoms; Z is $=O$; one of $R^1$ and $R^2$ is $=O$, $-OH$ or a $-O(CO)R^6$ group, and the other one is $-OH$ or $-O(CO)R_6$, or $R_1$ is $=O$ and $R_2$ is H, wherein $R^6$ is a saturated or unsaturated acyclic hydrocarbon group having from 1 to about 20 carbon atoms, or $-(CH_2)mR_7$ wherein m is 0 or an integer of from 1 to 10, and $R_7$ is cycloalkyl radical, having from three to seven carbon atoms, or a hydrocarbyl aryl or heteroaryl radical, as defined above in free form or a pharmaceutically acceptable salt thereof.

These and other aspects of the invention will become apparent from the description of the invention which follows below.

BRIEF DESCRIPTION OF THE DRAWING FIGURE

The FIGURE shows the effect on the eyelashes of one patient treated for glaucoma with Lumigan® bimatoprost for six months.

DETAILED DESCRIPTION OF THE PREFERRED EMBODIMENT

Alopecia (baldness) a deficiency of either normal or abnormal hair, is primarily a cosmetic problem in humans. It is a deficiency of terminal hair, the broad diameter, colored hair that is readily seen. However, in the so-called bald person although there is a noticeable absence of terminal hair, the skin does contain vellus hair which is a fine colorless hair which may require microscopic examination to determine its presence. This vellus hair is a precursor to terminal hair. In accordance with the invention as described herein, compounds represented by

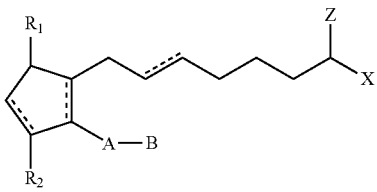

wherein $R_1$, $R_2$, A, B, Z and X are defined above, can be used to stimulate, such as stimulating the conversion of vellus hair to growth as terminal hair as well as increasing the rate of growth of terminal hair.

The present invention was discovered as follows:

In the course of treating patients having glaucoma, treatment may only be appropriate in one eye. Within the course of daily practice it was discovered that a patient who been treated with bimatoprost has lashes that were longer, thicker and fuller in the treated eye than in the non-treated eye. On examination the difference was found to be very striking. The lashes were longer and had a more full dense appearance in the treated eye. The lash appearance on the lids of the treated eye would have appeared quite attractive if it represented a bilateral phenomenon. Because of its asymmetric nature, the long lashes on one side could be construed as disturbing from a cosmetic standpoint. Because of the very unusual appearance a systematic examination of other patients who were taking bimatoprost in only one eye was made. It soon became apparent that this altered appearance was not an isolated finding. Comparison of the lids of patients who were taking bimatoprost in only one eye revealed subtle changes in the lashes and adjacent hairs of the bimatoprost-treated side in several patients. Definite differences could be identified to varying degrees in the lashes and adjacent hairs of all patients who were taking the drug on a unilateral basis for longer than 6 months.

These findings were totally unexpected and surprising. Minoxidil is thought to stimulate hair growth by its ability to cause vasodilation suggesting that agents with such a capability may be uniquely effective in stimulating hair growth. The finding that bimatoprost, which, as explained below, is not a prostaglandin derivative, such as latanoprost stimulates hair growth is especially surprising and unexpected.

The changes in the lashes were apparent on gross inspection in several patients once attention was focused on the issue. In those with light colored hair and lashes, the differences were only seen easily with the aid of the high magnification and lighting capabilities of the slit lamp biomicroscope. In the course of a glaucoma follow up examination, attention is generally immediately focused on the eye itself. Because of the high power magnification needed only one eye is seen at a time and the eye is seen at a high enough power that the lashes are not in focus. At these higher powers, any lash asymmetry between the two eyes is not likely to be noticed except by careful systematic comparison of the lashes and adjacent hairs of the eyelids of the two eyes.

Observed parameters leading to the conclusion that more robust hair growth occurred in the treated area following administration of bimatoprost were multiple. They included increased length of lashes, increased numbers of lashes along the normal lash line, increased thickness and luster of lashes, increased auxiliary lash-like terminal hair in transitional areas adjacent to areas of normal lash growth, increased lash-like terminal hairs at the medial and lateral canthal area, increased pigmentation of the lashes, increased numbers, increased length, as well as increased luster, and thickness of fine hair on the skin of the adjacent lid, and finally increased perpendicular angulation of lashes and lash-like terminal hairs. The conclusion that hair growth is stimulated by bimatoprost is thus supported not by evidence of a difference in a single parameter but is based on multiple parameters of hair appearance in treated vs. control areas in many subjects. This finding is entirely unexpected and represents a previously unrecognized effect of bimatoprost on stimulation of hair follicles. The modified hairs of the lashes normally turn over slowly and are in their resting phase longer than hair on, for example, the scalp. The ability to cause differences in appearance of lashes, the ability to stimulate conversion of vellus or intermediate hair to terminal hairs in transitional areas and the ability to stimulate growth of vellus hair on the skin indicates that bimatoprost is a diversely effective and efficacious agent for the stimulation of hair growth. Thus, the present invention provides a treatment by bimatoprost of hair of the scalp, eyebrows, beard and other areas that contain hair that results in increased hair growth in the corresponding areas.

Patients that are treated in or around the eye with compounds of the invention, such as bimatoprost, regularly develop hypertrichosis including altered differentiation, numbers, length, thickness, curvature and pigmentation in the region of treatment.

Some examples of representative compounds useful in the practice of the present invention include the compounds shown in Table 1:

TABLE 1 cyclopentane heptenamide-5-cis-2-(3α-hydroxy-5-phenyl-1-trans-pentenyl)-3,5-dihydroxy, [1α, 2β, 3α, 5,6α]
cyclopentane N,N-dimethylheptenamide-5-cis-2-(3α-hydroxy-5-phenyl-1-trans-pentenyl)-3,5-dihydroxy, [1α, 2β, 3α, 5α]
cyclopentane heptenylamide-5-cis-2-(3α-hydroxy-4-meta-chlorophenoxy-1-trans-pentenyl)-3,5-dihydroxy, [1α, 2β, 3α, 5α]
cyclopentane heptenylamide-5-cis-2-(3α-hydroxy-4-trifluoromethyl-phenoxy-1-trans-pentenyl)-3,5-dihydroxy, [1α, 2β, 3α, 5α]
cyclopentane N-isopropyl heptenamide-5-cis-2-(3α-hydroxy-5-phenyl-1-trans-pentenyl)-3,5-dihydroxy, [1α, 2β, 3α, 5α]
cyclopentane N-ethyl heptenamide-5-cis-2-(3α-hydroxy-5-phenyl-1-trans-pentenyl)-3,5 dihydroxy, [1α, 2β, 3α, 5α]
cyclopentane N-methyl heptenamide-5-cis-2-(3α-hydroxy-5-phenyl-1-trans-pentenyl)-3,5-dihydroxy, [1α, 2β, 3α, 5α]
cyclopentane heptenamide-5-cis-2-(3α-hydroxy-4-meta-chlorophenoxy-1-trans-butenyl)-3,5-dihydroxy, [1α, 2β, 3α, 5α]

One presently preferred compound for use in the practice of the present invention is cyclopentane N-ethyl heptanamide-5-cis-2-(3α-hydroxy-5-phenyl-1-trans-pentenyl)-3,5-dihydroxy, [1α,2α,3α,5α], also known as bimatoprost and sold under the name of Lumigan® by Allergan, Inc., California, USA. This compound has the following structure:

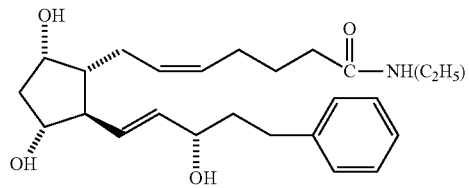

The synthesis of the above compounds described above has been disclosed in U.S. Pat. No. 5,607,978. This patent also shows, particularly in Examples 1, 2, 5 and 7 that these compounds are not prostaglandins, in that they do not behave as prostaglandins in art-recognized assays for prostaglandin activity. The invention thus relates to the use of the above compounds, or prodrugs of the active compounds, for treatment for the stimulation of hair growth. As used herein, hair growth includes hair associated with the scalp, eyebrows, eyelids, beard, and other areas of the skin of animals.

In accordance with one aspect of the invention, the compound is mixed with a dermatologically compatible vehicle or carrier. The vehicle which may be employed for preparing compositions of this invention may comprise, for example, aqueous solutions such as e.g., physiological salines, oil solutions or ointments. The vehicle furthermore may contain dermatologically compatible preservatives such as e.g., benzalkonium chloride, surfactants like e.g., polysorbate 80, liposomes or polymers, for example, methyl cellulose, polyvinyl alcohol, polyvinyl pyrrolidone and hyaluronic acid; these may be used for increasing the viscosity. Furthermore, it is also possible to use soluble or insoluble drug inserts when the drug is to be administered.

The invention is also related to dermatological compositions for topical treatment for the stimulation of hair growth which comprise an effective hair growth stimulating amount of one or more compounds as defined above and a dermatologically compatible carrier. Effective amounts of the active compounds may be determined by one of ordinary skill in the art but will vary depending on the compound employed, frequency of application and desired result, and the compound will generally range from about 0.0000001 to about 50%, by weight, of the dermatological composition, preferably. from about 0.001 to about 50%, by weight, of total dermatological composition, more preferably from about 0.1 to about 30%, by weight of the composition.

The present invention finds application in all mammalian species, including both humans and animals. In humans, the compounds of the subject invention can be applied for example, to the scalp, face, beard, head, pubic area, upper lip, eyebrows, and eyelids. In animals raised for their pelts, e.g., mink, the compounds can be applied over the entire surface of the body to improve the overall pelt for commercial reasons. The process can also be used for cosmetic reasons in animals, e.g., applied to the skin of dogs and cats having bald patches due to mange or other diseases causing a degree of alopecia.

The pharmaceutical compositions contemplated by this invention include pharmaceutical compositions suited for topical and local action.

The term "topical" as employed herein relates to the use of a compound, as described herein, incorporated in a suitable pharmaceutical carrier, and applied at the site of thinning hair or baldness for exertion of local action. Accordingly, such topical compositions include those pharmaceutical forms in which the compound is applied externally by direct contact with the skin surface to be treated. Conventional pharmaceutical forms for this purpose include ointments, liniments, creams, shampoos, lotions, pastes, jellies, sprays, aerosols, and the like, and may be applied in patches or impregnated dressings depending on the part of the body to be treated. The term "ointment" embraces formulations (including creams) having oleaginous, water-soluble and emulsion-type bases, e.g., petrolatum, lanolin, polyethylene glycols, as well as mixtures of these.

Typically, the compounds are applied repeatedly for a sustained period of time topically on the part of the body to be treated, for example, the eyelids, eyebrows, skin or scalp. The preferred dosage regimen will generally involve regular, such as daily, administration for a period of treatment of at least one month, more preferably at least three months, and most preferably at least six months.

For topical use on the eyelids or eyebrows, the active compounds can be formulated in aqueous solutions, creams, ointments or oils exhibiting physiologically acceptable osmolarity by addition of pharmacologically acceptable buffers and salts. Such formulations may or may not, depending on the dispenser, contain preservatives such as benzalkonium chloride, chlorhexidine, chlorobutanol, parahydroxybenzoic acids and phenylmercuric salts such as nitrate, chloride, acetate, and borate, or antioxidants, as well as additives like EDTA, sorbitol, boric acid etc. as additives. Furthermore, particularly aqueous solutions may contain viscosity increasing agents such as polysaccharides, e.g., methylcellulose, mucopolysaccharides, e.g., hyaluronic acid and chondroitin sulfate, or polyalcohol, e.g., polyvinylalcohol. Various slow releasing gels and matrices may also be employed as well as soluble and insoluble ocular inserts, for instance, based on substances forming in-situ gels. Depending on the actual formulation and compound to be used, various amounts of the drug and different dose regimens may be employed. Typically, the daily amount of compound for treatment of the eyelid may be about 0.1 ng to about 100 mg per eyelid.

For topical use on the skin and the scalp, the compound can be advantageously formulated using ointments, creams, liniments or patches as a carrier of the active ingredient. Also, these formulations may or may not contain preservatives, depending on the dispenser and nature of use. Such preservatives include those mentioned above, and methyl-, propyl-, or butyl-parahydroxybenzoic acid, betain, chlorhexidine, benzalkonium chloride, and the like. Various matrices for slow release delivery may also be used. Typically, the dose to be applied on the scalp is in the range of about 0.1 ng to about 100 mg per day, more preferably about 1 ng to about 10 mg per day, and most preferably about 10 ng to about 1 mg per day depending on the compound and the formulation. To achieve the daily amount of medication depending on the formulation, the compound may be administered once or several times daily with or without antioxidants.

The invention is further illustrated by the following non-limiting examples:

Example 1

In Vivo Treatment

A study is initiated to systematically evaluate the appearance of lashes and hair around the eyes of patients who are administering bimatoprost in only one eye. The study involves 10 subjects, 5 male, 5 female, average age 70 years, (ranging from 50-94 years). All patients have glaucoma. Each subject is treated daily by the topical application of one drop of bimatoprost at a dosage of 1.5.mu.g/ml/eye/day (0.03%, by weight, ophthalmic solution, sold under the name Lumigan® by Allergan, Irvine, Calif., U.S.A.) to the region of one eye by instilling the drop onto the surface of the eye. The region of the fellow control eye is not treated with bimatoprost and served as a control.

In the course of treatment with eye drops, there is typically spontaneous tearing, and excess fluid from the drops and associated tears gathers at the lid margins. In the course of wiping the drug containing fluid from the lid margins and adjacent lid, a thin film of the fluid is routinely spread to contact the adjacent skin of the lid area. This widespread exposure of the skin around the lid to the effect of drops is regularly demonstrated in patients who develop a contact dermatitis. Typically the entire area of the upper and lower lid are involved with induration, erythema and edema demonstrating the regular extensive exposure of the ocular adnexa to the influence of topically applied drugs.

The study is limited to subjects who have administered bimatoprost to one eye for more than 3 months. The mean duration of exposure to bimatoprost prior to assessing the parameter of lash growth between the control and study eye is 129 days (range 90-254 days). Observations are made under high magnification at the slit lamp biomicroscope. Documentation of differences between the control and treatment areas is accomplished using a camera specially adapted for use with the slit lamp biomicroscope.

The results of the observations are as follows:

Length of lashes: Increased length of eyelashes is regularly observed on the side treated with bimatoprost. The difference in length varies from approximately 10% to as much as 30%.

Number of lashes: Increased numbers of lashes are observed in the treated eye of each patient. In areas where there are a large number of lashes in the control eye, the increased number of lashes in the bimatoprost-treated eye gave the lashes on the treated side a more thickly matted overall appearance.

Auxiliary lash-like hair growth: Several patients have an apparent increase in lash-like hair in transitional areas adjacent to areas of normal lash distribution. These prominent robust appear lash-like hairs appeared to be of comparable length to the actual lashes. These long, thick lash-like hairs were present in the central portion of the lids of several patients in a linear arrangement just above the lash line. Hairs are present at similar locations in the control eyes but are by contrast thinner or more fine in appearance, have less luster and pigment and are more flat against the skin of the lid typical of vellus or intermediate hairs. In several patients, lash-like terminal hairs grow luxuriantly in the medial canthal area in the treated eye. In the corresponding control eye, vellus hairs are seen at the same location. Lash-like hairs are also present in the lateral canthal area of the treated eye but not the control eye in several subjects. Large lashes are not normally present at the lateral canthus and the area is generally free of all but a few occasional very fine lashes or vellus hairs.

Increased growth of vellus hair on lids: Fine microscopic vellus hair is present on the skin of the lids and is easily seen with the slit lamp biomicroscope. This vellus hair is typically denser adjacent to and below the lateral portion of the lower lids. While remaining microscopic, vellus hairs are increased in number, appear more robust and are much longer and thicker in treated than in control eyes in the areas below and lateral to the lower lid.

Perpendicular angulation of hairs: In areas where there are lash-like hairs above the lash line and in the medial and lateral canthal areas, the hairs are much longer, thicker and heavier. They also leave the surface of the skin at a more acute angle, as though they are stiffer or held in a more erect position by more robust follicles. This greater incline, pitch, rise or perpendicular angulation from the skin surface gives the appearance of greater density of the hairs.

The foregoing observations clearly establish that bimatoprost can be used to increase the growth of hair in man. This conclusion is based on the regular and consistent finding of manifestations of increased hair growth in treated vs. control areas in human subjects. The conclusion that the drug bimatoprost is capable of inducing increased robust growth of hair is based not on a single parameter, i.e., length, but is based on multiple lines of evidence as described in the results. Detailed examination and description of multiple parameters of differences in hair is greatly facilitated by the ability to examine the hairs at high magnification under stable conditions of fixed focal length and subject position utilizing the capabilities of the slitlamp biomicroscope.

The FIGURE shows the actual results on the eyelashes of a patient treated for glaucoma with Lumigan® bimatoprost for 6 months.

Example 2

Topical Cream

A topical cream is prepared as follows: Tegacid and spermaceti are melted together at a temperature of 70-80° C. Methylparaben is dissolved in about 500 gm of water and propylene glycol, polysorbate 80, and bimatoprost are added in turn, maintaining a temperature of 75-80° C. The methylparaben mixture is added slowly to the Tegacid and spermaceti melt, with constant stirring. The addition is continued for at least 30 minutes with additional stirring until the temperature has dropped to 40-45° C. Finally, sufficient water is added to bring the final weight to 1000 gm and the preparation stirred to maintain homogeneity until cooled and congealed.

Example 3

Topical Cream

A topical cream is prepared as follows: Tegacid and spermaceti are melted together at a temperature of 70-80° C. Methylparaben is dissolved in water and propylene glycol, polysorbate 80, and bimatoprost are added in turn, maintaining a temperature of 75-80° C. The methylparaben mixture is added slowly to the Tegacid and spermaceti melt, with constant stirring. The addition is continued for at least 30 minutes with additional stirring until the temperature has dropped to 40-45° C. Finally, sufficient water is added to bring the final weight to 1000 gm and the preparation stirred to maintain homogeneity until cooled and congealed.

The composition is applied to bald human scalp once daily to stimulate the growth of hair.

Example 4

Topical Ointment

An ointment containing 2% by weight bimatoprost is prepared as follows:

White petrolatum and wool fat are melted, strained and liquid petrolatum is added thereto. The bimatoprost, zinc oxide, and calamine are added to the remaining liquid petrolatum and the mixture milled until the powders are finely divided and uniformly dispersed. The mixture is stirred into the white petrolatum, melted and cooled with stirring until the ointment congeals.

The foregoing ointment can be applied topically to mammalian skin for increased rate of hair growth, and can be prepared by omitting the zinc oxide and calamine.

Example 5

Ointment

A dermatological ophthalmic ointment containing 10% by weight bimatoprost is prepared by adding the active compound to light liquid petrolatum. White petrolatum is melted together with wool fat, strained, and the temperature adjusted to 45-50° C. The liquid petrolatum slurry is added and the ointment stirred until congealed. Suitably the ointment is packaged in 30 gm tubes.

The foregoing ointment can be applied to the eyelid to enhance the growth of eyelashes. Similarly the composition can be applied to the brow for eyebrow growth.

Example 6

Solution

An aqueous solution containing 5%, by weight, bimatoprost is prepared as follows. Bimatoprost is dissolved in water and the resulting solution is sterilized by filtration. The solution is aseptically filled into sterile containers.

The composition so prepared can be used in the topical treatment of baldness by application to the scalp daily.

Example 7

Lotion

A sample of bimatoprost is dissolved in the vehicle of N-methylpyrrolidone and propylene glycol. The composition can be used for application to dogs or cats having hair loss due to mange or alopecia of other causes.

Example 8

Aerosol

An aerosol containing approximately 0.1% by weight bimatoprost is prepared by dissolving the bimatoprost in absolute alcohol. The resulting solution filtered to remove particles and lint. This solution is chilled to about minus 30° C. To the solution is added a chilled mixture of dichlorodifluoromethane and dichlorotetrafluoroethane.

Thirteen ml plastic-coated amber bottles are cold filled with 11.5 gm each of the resulting solution and capped.

The composition can be sprayed on the scalp daily to stimulate the growth of hair.

Example 9

Dusting Powder

A powder of the compound bimatoprost is prepared by mixing in dry form with talcum powder at a weight/weight ratio of 1:10. The powdered mixture is dusted on the fur of minks or other commercially valuable fur bearing animals and show animals for increased rate of hair growth.

Example 10

Related Compounds

Following the procedure of the preceding Examples, compositions are similarly prepared substituting an equimolar amount of a compound of Table 1 for the bimatoprost disclosed in the preceding Examples. Similar results are obtained.

While the preferred embodiment of the invention has been illustrated and described, it will be appreciated that various changes can be made therein without departing from the spirit and scope of the invention.

The embodiments of the invention in which an exclusive property or privilege is claimed are defined as follows:

What is claimed is:

1. A method for treating eyelashes, the method comprising topically administering a bimatoprost solution to an eyelid margin, wherein administration of the bimatoprost solution to the eyelid margin causes an increase in one or more eyelash attributes selected from the group consisting of length, thickness, and darkness.

2. The method of claim 1, wherein the administration causes an increase in eyelash length.

3. The method of claim 1, wherein the administration causes an increase in eyelash thickness.

4. The method of claim 1, wherein the administration causes an increase in eyelash darkness.

5. The method of claim 1, wherein the bimatoprost solution has a concentration of 0.03% by weight.

6. The method of claim 1, wherein the bimatoprost solution has a concentration of about 0.001% to about 5% by weight.

7. The method of claim 1, wherein the bimatoprost solution has a concentration of 0.03% by weight and administration thereof causes an increase in eyelash darkness.

8. The method of claim 7, wherein the bimatoprost solution is administered to an upper eyelid margin.

9. The method of claim 1, wherein the bimatoprost solution is administered to a lower eyelid margin.

10. The method of claim 7, wherein the bimatoprost solution is administered once daily.

11. A method of topically administering a bimatoprost solution, the method comprising applying a 0.03% by weight bimatoprost solution to an eyelid margin, wherein application of the bimatoprost solution causes increased darkness of the eyelashes on the eyelid margin where the bimatoprost solution is applied.

12. The method of claim 11, wherein administration of the bimatoprost solution further causes an increase in at least one eyelash attribute selected from the group consisting of eyelash length and eyelash thickness.

13. The method of claim 11, wherein the bimatoprost solution is applied to the eyelid margin once daily.

14. A method of treating eyelashes, the method comprising topically applying a 0.03% by weight bimatoprost solution to an upper eyelid margin, wherein once-daily application of the bimatoprost solution causes an increase in eyelash darkness on the eyelid margin where the bimatoprost solution is applied.

15. A method of treating eyelashes, the method comprising administering to an eyelid margin an effective amount of a solution containing about 0.03% by weight of bimatoprost, wherein administering the solution increases eyelash darkness on the eyelid margin where the solution is applied.

16. The method of claim 15, wherein the solution is administered to an upper eyelid margin.

17. The method of claim 15, wherein the solution is administered one time per day.

18. The method of claim 15, wherein administering the solution increases eyelash length.

19. The method of claim 15, wherein administering the solution increases eyelash thickness.

20. The method as in any one of claims 15-19, wherein the solution contains 0.03% by weight of bimatoprost.

* * * * *